United States Patent [19]

Schickaneder et al.

[11] Patent Number: 4,816,455

[45] Date of Patent: Mar. 28, 1989

[54] CRYSTALLINE, ANHYDROUS SIGMA-FORM OF 2-(4-(2-FUROYL)-(2-PIPERAZIN)-1-YL)-4-AMINO-6,7-DIMETHOXY-QUINAZOLINE HYDROCHLORIDE AND A PROCESS FOR ITS PREPARATION

[75] Inventors: Helmut Schickaneder, Eckental; Ingomar Grafe; Kurt H. Ahrens, both of Nuremberg, all of Fed. Rep. of Germany

[73] Assignee: Heumann Pharma GmbH & Co., Nuremberg, Fed. Rep. of Germany

[21] Appl. No.: 21,161

[22] Filed: Mar. 3, 1987

[30] Foreign Application Priority Data

Mar. 21, 1986 [EP] European Pat. Off. ........ 86103925.3

[51] Int. Cl.$^4$ .................... A61K 31/505; C07D 405/14
[52] U.S. Cl. ..................................... 514/254; 544/291
[58] Field of Search ........................ 544/291; 514/254

[56] References Cited

U.S. PATENT DOCUMENTS

| 4,026,894 | 5/1977 | Winn et al. | 544/291 |
| 4,092,315 | 5/1978 | Bianco | 544/291 |
| 4,251,532 | 2/1981 | Bateman | 544/291 |

FOREIGN PATENT DOCUMENTS 900925 2/1985 Belgium .

OTHER PUBLICATIONS

Lehmann et al., "Chemical Abstracts", vol. 95, 1981, Col. 95:62250b.
Lehmann et al., "Chemical Abstracts", vol. 101, 1984, Col. 101:90971y.
Lehmann et al., "Chemical Abstracts", vol. 101, 1984, Col. 101:230571v.
Lehmann et al., "Chemical Abstracts", vol. 102; 1985, Col. 102:62270w.
Lindholm, "Chemical Abstracts", vol. 103, 1985, Col. 103:11460w.
Lehmann et al., "Chemical Abstracts", vol. 106, 1987, Col. 106:33113z.

*Primary Examiner*—Glennon H. Hollrah
*Assistant Examiner*—James H. Turnipseed
*Attorney, Agent, or Firm*—Burns, Doane, Swecker & Mathis

[57] ABSTRACT

A new anhydrous crystalline form of prazosine hydrochloride characterized by the following bands in the infra-red spectrum in potassium bromide is described:
3445 cm$^{-1}$ (2.90 μm),
1010 cm$^{-1}$ (9.90 μm) (duplet), and
768 cm$^{-1}$ (13.03 μm).

This new form is distinguished by its surprisingly great stability in storage compared with known polymorphous forms of prazosine.

3 Claims, 1 Drawing Sheet

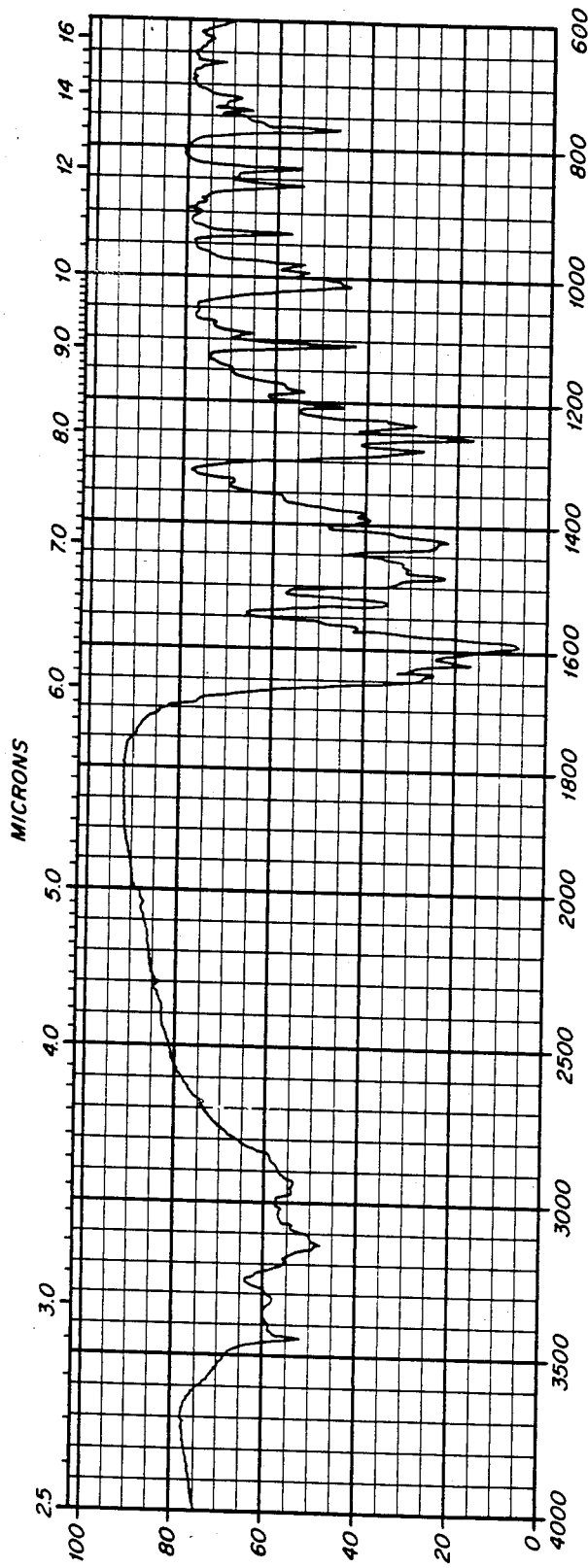

CRYSTALLINE, ANHYDROUS SIGMA-FORM OF 2-(4-(2-FUROYL)-(2-PIPERAZIN)-1-YL)-4-AMINO-6,7-DIMETHOXY-QUINAZOLINE HYDROCHLORIDE AND A PROCESS FOR ITS PREPARATION

DESCRIPTION

This invention relates to a new anhydrous, stable, crystalline form of 2-[4-(2-furoyl)-(2-piperazin)-1-yl]-4-amino-6,7-dimethoxyquinazoline hydrochloride (prazosine hydrochloride). Prazosine hydrochloride is a known antihypertensive agent corresponding to the following formula:

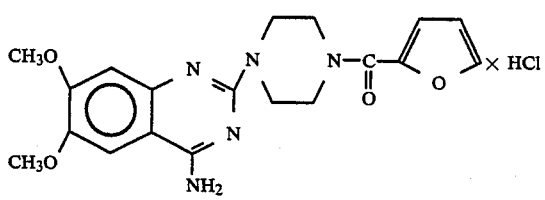

This active ingredient was first described in U.S. Pat. No. 3,511,836.

Various polymorphic forms of prazosine hydrochloride have since become known. DE-AS No. 2 708 192 describes the α-form, the β-form, the γ-form, a polyhydrate/dihydrate, the monohydrate, the δ-form and a methanolate. According to the said document, the individual forms have certain characteristic IR bands and characteristic peaks in the diffraction diagram. According to DE-AS No. 2 708 192, the α-form of prazosine hydrochloride has distinct advantages for handling, storage and the preparation of formulations by virtue of its stability and comparative lack of hygroscopic character.

Another crystalline form of prazosine hydrochloride is described in DE-OS No. 3 429 415, in which the substance described there as the δ-form is said to be relatively non-hygroscopic. On the basis of the characteristic bands in the infra-red spectrum given in the said document, it may be assumed that the δ-form of DE-OS No. 3 429 415 is identical to the δ-form of prazosine hydrochloride described in DE-AS No. 2 708 192.

It is an object of the present invention to provide a new, hitherto unknown, exceptionally stable and always reproducible crystalline form of prazosine hydrochloride.

The invention solves this problem by providing the δ-form of prazosine hydrochloride. The δ-form according to the invention is characterised by a characteristic infra-red spectrum in potassium bromide with absorption bands at the wavelengths or frequencies shown in the following Table.

TABLE

| | Characteristic bands | |
|---|---|---|
| μm | cm$^{-1}$ | |
| 2.90 | 3445 | singlet (sharp) |
| 9.90 | 1010 | duplet |
| 13.03 | 768 | singlet (sharp) |

The new crystalline, anhydrous δ-form of prazosine hydrochloride may be obtained according to the invention by a process in which (a) 2-[4-(2-furoyl)-(2-piperazin)-1-yl]-4-amino-6,7-dimethoxyquinazoline (prazosine base) corresponding to formula I

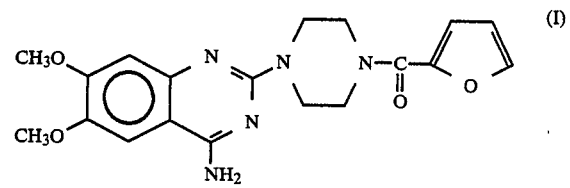

is reacted stepwise by an aqueous acid-base reaction;

(b) the thoroughly dried δ-form of prazosine hydrochloride hydrate obtained, corresponding to formula II

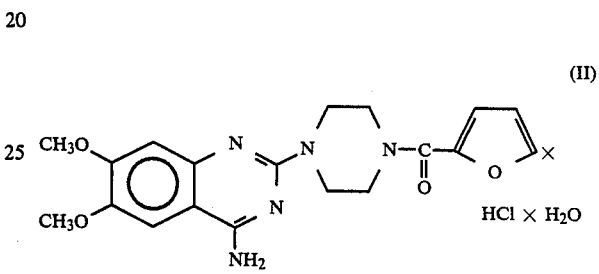

is reacted in methanol; and (c) the resulting δ-form of prazosine hydrochloride methanolate corresponding to formula III

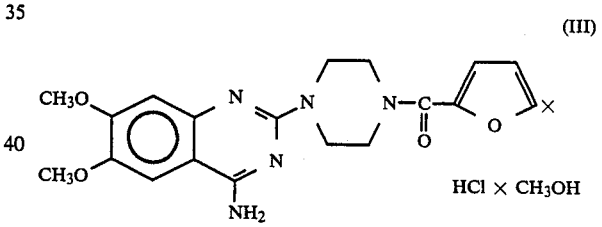

is then dried.

The individual stages of this process are described in detail below.

I. Stage (a)

In the first stage, 2-[4-(2-furoyl)-(2-piperazin)-1-yl]-4-amino-6,7-dimethoxyquinazoline (prazosine base) corresponding to formula I

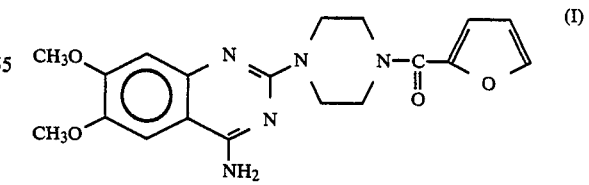

is reacted in a reaction solution at an elevated temperature, e.g. at 30° to 100° C., preferably at 75° C. The molar quantity of prazosine base put into the process is different from the molar quantity of glacial acetic acid, the two being preferably put into the process in a molar ratio of 1 to 2. The reaction solution preferably consists of methyl glycol, water and glacial acetic acid although the reaction may also be carried out with other polyglycols, e.g. a diethylene glycol, and water and weak organic acids such as formic acid, propionic acid, butyric acid, glycollic acid, glyceric acid, isobutyric acid, n-valeric acid or caproic acid. The reaction in methyl glycol, water and glacial acetic acid is, however, preferred.

The reaction mixture is subsequently reacted with an equimolar or, preferably, excess molar quantity (e.g. a 30% excess) of aqueous ammonium chloride solution, based on the quantity of prazosine base, at an elevated temperature, e.g. at 30° to 100° C., preferably at 80° to 90° C. The reaction time is 10 to 60 minutes, e.g. about 30 minutes. The product obtained is dried very thoroughly, for example in a vacuum at 100° C.

II. Stage (b)

In the second stage, the thoroughly dried δ-form of prazosine hydrochloride hydrate reacts in methanol with 5 to 60 minutes, preferably in 30 minutes, at a temperature from 20° C. to the reflux temperature of the solvent, preferably at the reflux temperature, to be converted into the δ-form of prazosine hydrochloride methanolate.

III. Stage (c)

The δ-form of prazosine hydrochloride methanolate is converted into the anhydrous prazosine hydrochloride δ-form according to the invention by removal of the crystalline methanol component.

At this stage, drying of the δ-form of prazosine hydrochloride methanolate is preferably carried out in a vacuum at about 90° to 120° C., preferably at 105°–110° C., and takes about 4 to 20 hours, preferably 15 hours.

The new form of prazosine hydrochloride according to this invention is found to have an unexpectedly increased stability compared with the polymorphous forms of this active ingredient hitherto known. This has been demonstrated by stability tests in which the δ-form of prazosine hydrochloride according to the invention was tested under various storage conditions. For example, samples were stored at 45° C., 55° C. and 75° C. for 12 weeks and then analyzed from their IR spectra and by means of high pressure liquid chromatography (determination of contents). No visual changes in the samples were observed even after three weeks' storage in daylight.

The investigation of various samples in aqueous suspension at pH values from 1 to 10 over a period of 6 weeks with and without exposure to daylight at temperatures of 45° C., 55° C. and 75° C. (12 weeks' duration) showed no visual changes. The parameters of the quantitative determinations were also unchanged.

Comparison tests showed that the new δ-form of prazosine hydrochloride according to the invention is superior in its stability to the α-form of prazosine hydrochloride disclosed in DE-AS 2 708 192.

The new δ-form of prazosine hydrochloride according to the invention is not hygroscopic. This means that even after prolonged storage, the water content of the new form according to the invention is not greater than 1.5%.

The δ-form of prazosine hydrochloride according to this invention containing up to but not significantly more than about 1.5% of water is here regarded as anhydrous.

The invention will now be explained with reference to the FIGURE and the following Examples. The FIGURE represents the infra-red spectrum of the δ-form of prazosine hydrochloride according to the invention.

EXAMPLE 1

(a) δ-Form of prazosine hydrochloride hydrate 2.4 kg (6.53 mol) of prazosine base are suspended in 9 l of methylglycol, 8.5 l of water and 7 l (12.2 mol) of glacial acetic acid in a 50 l reactor and heated to about 75° C. until solution has set in. 100 g of Tonsil and 100 g of active charcoal are added to the reaction solution and the solution is passed through a filter heated to about 90° to 100° C. into a 100 liter reaction tank.

A hot solution (about 80° to 90° C.) of 450 g (8.4 mol) of ammonium chloride in about 15 l of water is added to the filtrate within 10 minutes to precipitate the prazosine hydrochloride. The reaction mixture is then stirred for about 15 minutes and cooled to 20° C. The product is suction filtered and then washed, first with about 2.5 l of water and then with 2.5 l of methanol. After the product has been pressed to remove moisture, it is dried very thoroughly at 100° C. in a vacuum.

Yield of δ-form of prazosine hydrochloride hydrate after drying: 1.9 kg.

(b) δ-form of prazosine hydrochloride methanolate

The dried form of hydrate obtained (1.9 kg) is introduced into 7.6 l of methanol and heated to the reflux temperature for about 30 minutes. The reaction mixture is then suction filtered and the product is washed with 1.9 l of methanol.

2.0 kg of the δ-form of prazosine hydrochloride methanolate are obtained after drying in air.

$C_{19}H_{21}N_5O_4 \cdot HCl \cdot CH_3OH$ (451.5): Calculated: C 53.15, H 5.80, N 15.50, Cl 7.85. Found: C 53.10, H 5.71, N 15.38, Cl 7.81.

Melting point (determined by DTA): 265° C. (decomposition); elimination of methanol occurs at 110°–160° C.

Remark: The methanolate form of α-prazosine melts with decomposition at 275° C.

EXAMPLE 2

δ-Form of prazosine hydrochloride 2.0 kg of the δ-form of prazosine hydrochloride methanolate are dried in a vacuum (10 mbar) at 105° to 110° C. for 15 hours.

Yield: 1.7 kg (61%, based on the prazosine base).

Melting point (determined by DTA): 265° C. (decomposition).

IR: (KRr$^{-1}$) $\gamma$=3445 cm$^{-1}$, 1010 cm$^{-1}$, 768 cm$^{-1}$ (characteristic bands).

$C_{19}H_{21}N_5O_4 \cdot HCl$ (419.5): Calculated: C 54.34, H 5.28, N 16.68, Cl 8.44. Found: C 54.31, H 5.22, N 16.60, Cl 8.32.

Remark: α-Prazosine melts with decomposition at 275° C.

We claim:

1. The crystalline, anhydrous δ-form of 2-[4-(2-furoyl)-(2-piperazin)-1-yl]-4-amino-6,7-dimethoxyquinazoline hydrochloride, characterized by an infrared spectrum in potassium bromide with absorption bands at the following frequencies or wavelengths:
   3445 cm$^{-1}$ (2.90 μm),
   1010 cm$^{-1}$ (9.90 μm) (duplet) and
   768 cm$^{-1}$ (13.03 μm).

2. Process for the preparation of the δ-form of 2-[4-(2-furoyl)-(2-piperazin)-1-yl]-4-amino-6,7-dimethoxyquinazoline hydrochloride according to claim 1, characterised in that 2-[4-(2-furoyl)-(2-piperazin)-1-yl]-4- amino-6,7-dimethoxyquinazoline is reacted stepwise by an aqueous acid-base reaction and then dried and the dried δ-form of 2-[4-(2-furoyl)-(2-piperazin)-1-yl]-4-amino-6,7-dimethoxyquinazoline hydrochloride hydrate obtained is reacted in methanol and that the resulting δ-form of 2-[4-(2-furoyl)-(2-piperazin)-1-yl]-4-amino-6,7-dimethoxyquinazoline hydrochloride methanolate is dried with removal of the crystalline methanol component.

3. Pharmaceutical preparation, characterised in that it contains the crystalline, anhydrous δ-form of 2-[4-(2-furoyl)-(2-piperazin)-1-yl]-4-amino-6,7-dimethoxyquinazoline hydrochloride according to claim 1 in addition to the usual auxiliary agents and carriers.

* * * * *

UNITED STATES PATENT AND TRADEMARK OFFICE
CERTIFICATE OF CORRECTION

PATENT NO. : 4,816,455
DATED : March 28, 1989
INVENTOR(S) : Helmut Schickaneder, et al It is certified that error appears in the above-indentified patent and that said Letters Patent is hereby corrected as shown below:

Column 4, line 3, delete "$\delta$" and insert --$\sigma$--.

Column 4, line 21, delete "$\delta$" and insert --$\sigma$--.

Column 4, line 23, delete "$\delta$" and insert --$\sigma$--.

Column 4, line 29, delete "$\delta$" and insert --$\sigma$--.

Column 4, line 49, delete "KRr$^{-1}$" and insert --"KBr$^{-1}$"--.

Claim 2, at column 5, line 3, delete "$\delta$" and insert --$\sigma$--.

Signed and Sealed this

Sixth Day of December, 1994

Attest:

BRUCE LEHMAN

*Attesting Officer*    *Commissioner of Patents and Trademarks*

UNITED STATES PATENT AND TRADEMARK OFFICE
CERTIFICATE OF CORRECTION

PATENT NO. : 4,816,455

DATED : March 28, 1989

INVENTOR(S) : Helmut Schickaneder et al

It is certified that error appears in the above-identified patent and that said Letters Patent is hereby corrected as shown below:

Column 1, line 54, delete "$\delta$" and insert --$\sigma$--, both occurrences.

Column 2, line 1, delete "$\delta$" and insert --$\sigma$--.

Column 2, line 17, delete "$\delta$" and insert --$\sigma$--.

Column 2, line 32, delete "$\delta$" and insert --$\sigma$--.

Column 3, line 15, delete "$\delta$" and insert --$\sigma$--.

Column 3, line 21, delete "$\delta$" and insert --$\sigma$--.

Column 3, line 24, delete "$\delta$" and insert --$\sigma$--.

Column 3, line 26, delete "$\delta$" and insert --$\sigma$--.

Column 3, line 28, delete "$\delta$" and insert --$\sigma$--.

Column 3, line 36, delete "$\delta$" and insert --$\sigma$--.

Column 3, line 52, delete "$\delta$" and insert --$\sigma$--.

Column 3, line 56, delete "$\delta$" and insert --$\sigma$--.

Column 3, line 61, delete "$\delta$" and insert --$\sigma$--.

Column 3, line 67, delete "$\delta$" and insert --$\sigma$--.

Column 4, line 42, delete "$\delta$" and insert --$\sigma$--.

Column 4, line 43, delete "$\delta$" and insert --$\sigma$--.

UNITED STATES PATENT AND TRADEMARK OFFICE
CERTIFICATE OF CORRECTION

PATENT NO. : 4,816,455
DATED : March 28, 1989
INVENTOR(S) : Helmut Schickaneder et al It is certified that error appears in the above-identified patent and that said Letters Patent is hereby corrected as shown below:

Claim 1, at column 4, line 57, delete "$\delta$" and insert --$\sigma$--.
Claim 2, at column 4, line 65, delete "$\delta$" and insert --$\sigma$--.

Claim 2, at column 5, line 7, delete "$\delta$" and insert --$\sigma$--.
Claim 3, at column 6, line 4, delete "$\delta$" and insert --$\sigma$--.

Signed and Sealed this

Twenty-fifth Day of April, 1995

Attest:

BRUCE LEHMAN

Attesting Officer    Commissioner of Patents and Trademarks

REEXAMINATION CERTIFICATE (1853rd)

United States Patent [19]

Schickaneder et al.

[11] B1 4,816,455

[45] Certificate Issued  Nov. 24, 1992

[54] CRYSTALLINE, ANHYDROUS SIGMA-FORM OF 2-(4-(2-FUROYL)-(2-PIPERAZIN)-1-YL)-4-AMINO-6,7-DIMETHOXY-QUINOAZOLINE HYDROCHLORIDE AND A PROCESS FOR ITS PREPARATION

[75] Inventors: Helmut Schickaneder, Eckental; Ingomar Grafe; Kurt H. Ahrens, both of Nuremberg, all of Fed. Rep. of Germany

[73] Assignee: Heumann Pharma GmbH & Co.

Reexamination Request:
No. 90/002,455, Sep. 27, 1991

Reexamination Certificate for:
Patent No.: 4,816,455
Issued: Mar. 28, 1989
Appl. No.: 21,161
Filed: Mar. 3, 1987

[30] Foreign Application Priority Data

Mar. 21, 1986 [EP] European Pat. Off. ........ 86103925.3

[51] Int. Cl.$^5$ .................. A61K 31/505; C07D 405/14
[52] U.S. Cl. ...................................... 514/254; 544/291
[58] Field of Search .......................... 514/254; 544/291

[56] References Cited

U.S. PATENT DOCUMENTS

4,092,315  5/1978  Bianco ................................. 544/291
4,739,055  4/1988  Lindholm ........................... 544/291

*Primary Examiner*—Alan L. Rotman

[57] ABSTRACT

A new anhydrous crystalline form of prazosine hydrochloride characterized by the following bands in the infra-red spectrum in potassium bromide is described:
3445 cm$^{-1}$ (2.90 μm),
1010 cm$^{-1}$ (9.90 μm) (duplet), and
768 cm$^{-1}$ (13.03 μm).

This new form is distinguished by its surprisingly great stability in storage compared with known polymorphous forms of prazosine.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-3 is confirmed.

* * * * *